United States Patent [19]
Yoneda et al.

[11] Patent Number: 5,997,852
[45] Date of Patent: Dec. 7, 1999

[54] REMEDY FOR DERMATITIS

[75] Inventors: Akiko Yoneda; Hideaki Kitajima; Kenji Tsunoda; Kazuo Hasegawa; Takako Ishii, all of Tokyo, Japan

[73] Assignee: Taisho Pharmaceutical Co., Ltd., Tokyo, Japan

[21] Appl. No.: 08/875,142

[22] PCT Filed: Jan. 18, 1996

[86] PCT No.: PCT/JP96/00064

§ 371 Date: Oct. 8, 1997

§ 102(e) Date: Oct. 8, 1997

[87] PCT Pub. No.: WO96/22102

PCT Pub. Date: Jul. 25, 1996

[30] Foreign Application Priority Data

Jan. 18, 1995 [JP] Japan ................................. 7-005783
Apr. 6, 1995 [JP] Japan ................................. 7-081048

[51] Int. Cl.⁶ .................................................. A61K 7/06
[52] U.S. Cl. .......................................... 424/70.1; 424/401
[58] Field of Search ........................... 514/859; 424/401, 424/70.1

[56] References Cited

U.S. PATENT DOCUMENTS

| | | | |
|---|---|---|---|
| 4,273,763 | 6/1981 | Horrobin | 424/145 |
| 4,302,447 | 11/1981 | Horrobin | 424/145 |
| 4,309,415 | 1/1982 | Horrobin | 424/85 |
| 4,393,049 | 7/1983 | Horrobin | 424/145 |
| 4,415,554 | 11/1983 | Horrobin | 424/145 |
| 4,444,755 | 4/1984 | Horrobin | 424/145 |
| 4,931,468 | 6/1990 | Horrobin | 514/560 |
| 5,145,686 | 9/1992 | Horrobin | 424/677 |
| 5,252,333 | 10/1993 | Horrobin | 424/422 |
| 5,324,748 | 6/1994 | Horrobin | 514/560 |
| 5,650,157 | 7/1997 | Bockow | 424/401 |

FOREIGN PATENT DOCUMENTS

| | | | |
|---|---|---|---|
| 0 085 579 | 8/1983 | European Pat. Off. | A61K 45/06 |
| 0 139 480 | 5/1985 | European Pat. Off. | A61K 35/04 |
| 54-117035 | 9/1979 | Japan | A61K 33/30 |
| 55-27168 | 2/1980 | Japan | A61K 31/20 |
| 58-23629 | 2/1983 | Japan | A61K 35/78 |
| 58-208217 | 12/1983 | Japan | A61K 31/19 |
| 60-94913 | 5/1985 | Japan | A61K 34/04 |

OTHER PUBLICATIONS

International Search Report.

*Primary Examiner*—Thurman K. Page
*Assistant Examiner*—William E. Benston, Jr.
*Attorney, Agent, or Firm*—Sughrue, Mion, Zinn, Macpeak & Seas, PLLC

[57] ABSTRACT

A dermatitis-curing agent, characterized by comprising (A) a zinc compound and (B) at least one compound selected from the group consisting of multivalent unsaturated fatty acids and their esters as effective components is very effective for enteropathic acrodermatitis syndrome, and seborrheic dermatitis, psoriasis vulgaris, bullous dermatitis and puritus cutaneus, which show similar skin symptoms, or for symtoms due to zinc deficiency caused by injuries, burn injuries and frostbites.

1 Claim, 3 Drawing Sheets

REMEDY FOR DERMATITIS

TECHNICAL FIELD

The present invention relates to a dermatitis-curing agent.

BACKGROUND ART

Zinc (Zn) is a trace element contained in a high concentration next to iron throughout all the tissues and body fluids of human beings.

Physiological actions of zinc relate to, for example, growth, skeleton growth, activation of metabolism of skin and its related organs, maintenance of reproductive functions, maintenance of gustatory sensation and olfactory sensation, effects on mental conditions and action, improvement of immunological functions, etc.

Enteropathic acrodermatitis syndrome known as a recessive hereditary disease, whose main symptom is a characteristic tetter, is obviously due to zinc deficiency. Furthermore, it is reported that in the long-term intravenous zinc-deficient nutrition practice similar symptom to enteropathic acrodermatitis syndrome appears. Still furthermore, it is confirmed and reported that even in skin diseases showing common observations to those of enteropathic acrodermatitis syndrome, such as seborrheic dermatitis, psoriasis vulgaris, bullous dermatitis, pruritus cutaneus, etc. or even in case of injuries, burn injuries, frostbites, a blood zinc concentration is lowered, often resulting in zinc deficiency.

It is known, on the other hand, that when zinc is excessively taken in, there occur diarrhea, stomach erosion, decrease in plasma HDL cholesterol, etc. and in serious cases there occurs dehydration.

Fatty acids having 16 to 22 carbon atoms and at least two double bonds such as linoleic acid, γ-linolenic acid, eicosapentaenoic acid (EPA), docosahexaenoic acid (DHA), arachidonic acid (Ara), dihomo-γ-linolenic acid (DGLA), etc. are called generally multivalent unsaturated fatty acids, and constitute cell membranes as major components and furthermore take part in control of membrane fluidity, etc. Still furthermore, they have an antilipotropic action, an antiinflammatory action and an antithrombotic action. Still furthermore, they are important precursors for prostaglandins (PG) having functions to control an immunological system, a circulatory system, a hormone secretory system, etc.

There are many reports that linoleic acid has an action to retain water in the skin and effects on prevention of adult diseases caused by excessive intake of animal fat containing a large amount of saturated fatty acids as one factor, such as an action to lower a blood cholesterol concentration, an anti-cancer action, etc.

It is reported that γ-linolenic acid has a stronger action to lower a blood cholesterol concentration than linoleic acid, an anti-allergic action, an effect on atopic dermatitis, control of fatty liver due to alcohol intake, relief of menstruation pain, etc.

It is reported that EPA has many physiological functions such as an antithrombotic action, an antilipotropic action, a hypotensive action, an antiinflammatory action, an anti-allergic action, etc.

It is reported that DHA has physiological actions on the cranial nerve system such as an action to improve the visual acuity reduction, an effect on improvement of memory and learning ability, an essential component of mother's milk for brain growth, etc.

It is reported that Ara has physiological actions such as an action as an essential fatty acid, an action to suppress skin psoriasis, an action to protect the stomach wall, an action to lower a blood cholesterol concentration, a liver-protecting action such as prevention of fatty liver, etc., an important substance for growth of fetal bodies or brains, etc.

It is reported that DGLA has similar physiological actions to those of γ-linolenic acid and further has an action as a PG1 group precursor and such physiological actions as an antithrombotic action, a hypotensive action, an anti-dyskinesia action, etc.

DISCLOSURE OF THE INVENTION

The present inventors have found that dermatitis caused by zinc deficiency can be improved at a much less zinc dose by administering a combination of a zinc compound with a multivalent unsaturated fatty acid or its esters, and have established the present invention.

An object of the present invention is to provide an effective dermatitis-curing agent against enteropathic acrodermatitis syndrome, and skin diseases showing similar skin symptom such as seborrheic dermatitis, psoriasis vulgaris, bullous dermatitis and pruritus cutaneus or symptoms accompanied by zinc deficiency due to injuries, burn injuries and frostbites.

A dermatitis-curing agent according to the present invention is characterized by comprising (A) a zinc compound and (B) at least one compound selected from the group consisting of multivalent unsaturated fatty acids and their esters (which may be hereinafter referred to as "multivalent unsaturated fatty acids") as effective components.

Zinc compound for use in the present invention is organic acid salts or inorganic acid salts of zinc and specifically includes zinc sulfate, zinc gluconate, zinc chloride, zinc oxide, etc. Effective dose thereof is 1 to 50 mg, preferably 5 to 20 mg per day for a healthy adult as zinc contents.

Multivalent unsaturated fatty acid is fatty acids having 16 to 22 carbon atoms and at least two double bonds in the molecule, and preferably are linoleic acid, γ-linolenic acid, EPA, DHA, Ara and DGLA, more preferably EPA and DHA. Esters of multivalent unsaturated fatty acid include, for example, triacylglycerides, ethyl esters, etc. Effective daily dose of linoleic acid for a healthy adult is 100 mg to 35 g, preferably 300 mg to 20 g. Effective dose of γ-linolenic acid is 30 mg to 20 g, preferably 50 mg to 10 g. Effective dose each of other multivalent unsaturated fatty acids is 5 to 500 mg, preferably 20 to 250 mg.

In the present invention, mixing ratio by weight of zinc content to multivalent unsaturated fatty acid is 1:20 to 1:1000, preferably 1:20 to 1:200.

Zinc compound and multivalent unsaturated fatty acids as effective components of the present invention can be administered as they are, or, if desired, are mixed with other known additives, for example, a surfactant, a wetting agent, an antioxidant, a coloring agent, a corrigent, etc. and can be formulated into oral preparations such as capsules, liquid preparations, etc. according to the conventional method.

Surfactant includes, for example, glycerol, glycerol monostearate, monoglyceride, polyethylene hardened castor oil, polyoxyethylene hardened castor oil, sorbitan monostearate, sorbitan monopalmitate, sorbitan monolaurate, polyoxyethylene/polyoxypropylene block copolymer, polysolvates, methyl paraoxybenzoate, ethyl paraoxybenzoate, butyl paraoxybenzoate, propyl paraoxybenzoate, sodium laurylsulfate, macrogols, sucrose fatty acid ester, lecithine, magnesium metasilicate aluminate, etc.

Wetting agent includes, for example, diisobutyl adipate, light liquid paraffin, D-sorbitol, propylene glycol, etc.

Antioxidant includes, for example, dibutylhydroxytoluene (BHT), propyl gallate, butylhydroxyanisol (BHA), α-tocopherol, citric acid, etc.

Coloring agent includes, for example, tar colors, titanium oxide, etc.

Corrigent includes, for example, citric acid, adipic acid, ascorbic acid, menthol, purified sucrose, etc.

In case of liquid preparations, other physiologically active components, minerals, vitamins, amino acids, organ extracts, hormones, nutrients, perfumes, pH-adjusting agent, etc. can be added thereto to give an appropriate taste, if required.

Any additives as usually used in preparations can be supplemented, so long as they are pharmacologically acceptable.

Industrial Utility

The present dermatitis-curing agent is very effective for enteropathic acrodermatitis syndrome, and seborrheic dermatitis, psoriasis vulgaris, bullous dermatitis and pruritus cutaneus, which show similar skin symptoms, or for symptoms due to zinc deficiency caused by injuries, burn injuries and frostbites.

BEST MODE FOR CARRYING OUT THE INVENTION

Figure 1:
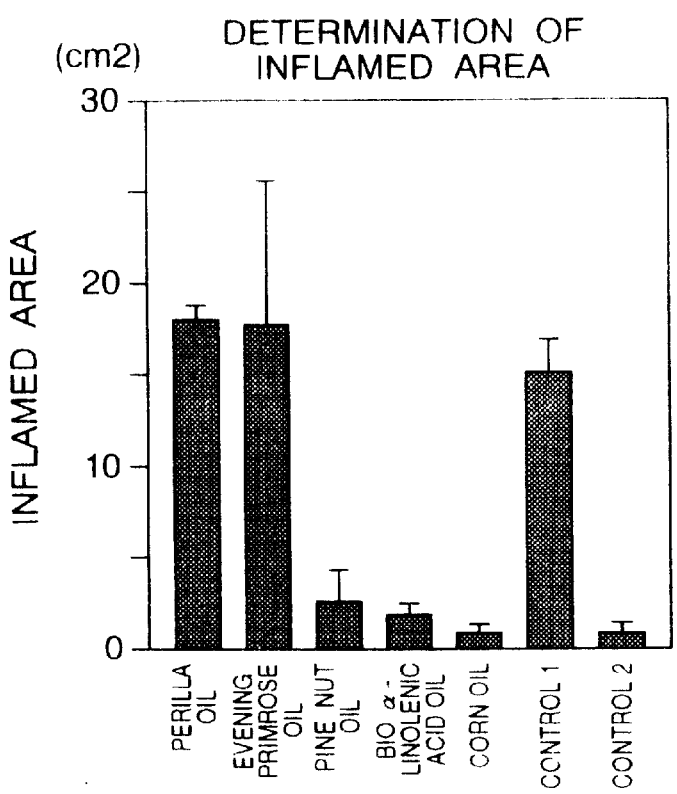
FIG. 1 is a diagram showing correlations between inflamed area of skin ($cm^2$) on the axis of ordinate and improvement ratios of skin inflammation as determined for individual drugs on the axis of abscissa.

The present invention will be described further in detail below, referring to Examples and Test Examples.

EXAMPLE 1

| (Formulation) | |
| --- | --- |
| Zinc gluconate (trihydrate) | 156.8 mg |
| Linoleic acid | 15 g |
| γ-linolenic acid | 5 g |

The foregoing compounds were mixed with 10 to 20 g of monoglyceride, polyethylene hardened castor oil, sucrose fatty acid ester or lecithine, or their mixture, 5 ml of ethanol and such an amount of distilled water as to make the total volume 100 ml in a mixer, and then the resulting mixture was emulsified in a homogenizer at 200 $kg/cm^3$ to make 100 ml of a liquid preparation.

EXAMPLE 2

| (Formulation) | |
| --- | --- |
| Zinc sulfate (heptahydrate) | 88.5 mg |
| Linoleic acid | 15 g |

The foregoing compounds were mixed with 5 to 15 g of monoglyceride, polyethylene hardened castor oil, sucrose fatty acid ester or lecithine, or their mixture, 3 ml of ethanol and such an amount of distilled water as to make the total volume 100 ml in a mixer, and then the resulting mixture was emulsified in a homogenizer at 200 $kg/cm^3$ to make 100 ml of a liquid preparation.

EXAMPLE 3

| (Formulation) | |
| --- | --- |
| Zinc gluconate (trihydrate) | 156.8 mg |
| Bio-γ-linolenic acid oil (containing 9.3 g of linoleic acid and 1.5 g of γ-linolenic acid) | 30 g |

The foregoing compounds were mixed with 10 to 30 g of monoglyceride, polyethylene hardened castor oil, sucrose fatty acid ester or lecithine, or their mixture, 5 ml of ethanol and such an amount of distilled water as to make the total volume 100 ml in a mixer, and then the resulting mixture was emulsified in a homogenizer at 200 $kg/cm^3$ to make 100 ml of a liquid preparation.

EXAMPLE 4

| (Formulation) | |
| --- | --- |
| Zinc sulfate (heptahydrate) | 88.5 mg |
| Bio-γ-linolenic acid oil | 20 g |

The foregoing compounds were mixed with 5 to 20 g of monoglyceride, polyethylene hardened castor oil, sucrose fatty acid ester or lecithins, or their mixture, 5 ml of ethanol and such an amount of distilled water to make the total volume 100 ml in a mixer, and then the resulting mixture was emulsified in a homogenizer at 200 $kg/cm^3$ to make 100 ml of a liquid preparation.

EXAMPLE 5

| (Formulation) | |
| --- | --- |
| Zinc gluconate (trihydrate) | 156.8 mg |
| Corn oil (containing 7.0 g of linoleic acid) | 20 g |

The foregoing compounds were mixed with 5 to 20 g of monoglyceride, polyethylene hardened caster oil, sucrose fatty acid ester or lecithine, or their mixture, 5 ml of ethanol and such an amount of distilled water as to make the total volume 100 ml in a mixer, and then the resulting mixture was emulsified in a homogenizer at 200 kg/cm$^3$ to make 100 ml of a liquid preparation.

EXAMPLE 6

(Formulation)

| | |
|---|---|
| Zinc sulfate (heptahydrate) | 88.5 mg |
| Pine nut oil (containing 5.7 g of linoleic oil) | 20 g |

The foregoing compounds were mixed with 5 to 20 g of monoglyceride, polyethylene hardened castor oil, sucrose fatty acid ester or lecithine, or their mixture, 5 ml of ethanol and such an amount of distilled water as to make the total volume 100 ml in a mixer, and then the resulting mixture was emulsified in a homogenizer at 200 kg/cm$^3$ to make 100 ml of a liquid preparation.

EXAMPLE 7

(Formulation)

| | |
|---|---|
| Zinc gluconate (trihydrate) | 156.8 mg |
| Evening primrose (*Oenothera tetraptera*) oil (containing 8.6 g of linoleic acid and 2.1 g of γ-linolenic acid) | 20 g |

The foregoing compounds were mixed with 5 to 20 g of monoglyceride, polyethylene hardened castor oil, sucrose fatty acid ester or lecithine, or their mixture, 5 ml of ethanol and such an amount of distilled water as to make the total volume 100 ml in a mixer, and then the resulting mixture was emulsified in a homogenizer at 200 kg/cm$^3$ to make 100 ml of a liquid preparation.

EXAMPLE 8

(Formulation)

| | |
|---|---|
| Zinc sulfate (heptahydrate) | 88.5 mg |
| Perilla (*Perilla ocimoides*) oil (containing 5.7 g of linoleic acid) | 20 g |

The foregoing compounds were mixed with 5 to 20 g of monoglyceride, polyethylene hardened castor oil, sucrose fatty acid ester or lecithine, or their mixture, 5 ml of ethanol and such an amount of distilled water as to make the total volume 100 ml in a mixer, and then the resulting mixture was emulsified in a homogenizer at 200 kg/cm$^3$ to make 100 ml of a liquid preparation.

EXAMPLE 9

(Formulation)

In 7 capsules,

| | |
|---|---|
| Zinc oxide | 25 mg |
| γ-Linolenic acid | 5000 mg |
| Magnesium metasilicate aluminate | 327 mg |
| Polysolvate 60 | 227 mg |
| Propylene glycol | 26 mg |

The foregoing compounds were weighed out and uniformly mixed. Then, 560 mg each of the resulting mixture was filled into soft elastic capsules or soft capsules to obtain 7 capsules.

EXAMPLE 10

(Formulation)

In ten capsules,

| | |
|---|---|
| Zinc oxide | 18.8 mg |
| Linoleic acid | 5000 mg |
| γ-Linolenic acid | 1500 mg |
| Magnesium metasilicate aluminate | 427 mg |
| Polysolvate 60 | 300 mg |
| Propylene glycol | 38 mg |

The foregoing compounds were weighed out and uniformly mixed. Then, 560 mg each of the resulting mixture was filled into soft elastic capsules or soft capsules to obtain 10 capsules.

EXAMPLE 11

(Formulation)

In 14 capsules,

| | |
|---|---|
| Zinc oxide | 6.3 mg |
| Linoleic acid | 5000 mg |
| γ-Linolenic acid | 1500 mg |
| Vitamin B$_2$ | 24 mg |
| Vitamin B$_6$ | 100 mg |
| Nicotinic acid amide | 60 mg |
| Vitamin C | 180 mg |
| Magnesium metasilicate aluminate | 470 mg |
| Polysolvate 60 | 330 mg |
| Propylene glycol | 42 mg |
| Wheat germ oil | 127.5 mg |

The foregoing compounds were weighed out and uniformly mixed. Then, 560 mg each of the resulting mixture was filled into soft elastic capsules or soft capsules to obtain 14 capsules.

EXAMPLE 12

(Formulation)

In 11 capsules,

| | |
|---|---|
| Zinc oxide | 6.3 mg |
| Linoleic acid | 5000 mg |
| Vitamin B$_2$ | 24 mg |
| Vitamin B$_6$ | 100 mg |
| Nicotinic acid amide | 60 mg |
| Vitamin C | 180 mg |
| Magnesium metasilicate aluminate | 370 mg |
| Polysolvate 60 | 260 mg |
| Propylene glycol | 33 mg |
| Wheat germ oil | 128 mg |

The foregoing compounds were weighed out and uniformly mixed. Then, 560 mg each of the resulting mixture was filled into soft elastic capsules or soft capsules to obtain 11 capsules.

EXAMPLE 13

(Formulation)

In 4 capsules,

| | |
|---|---|
| Zinc oxide | 6.3 mg |
| γ-Linolenic acid | 1500 mg |
| Vitamin B$_2$ | 24 mg |
| Vitamin B$_6$ | 100 mg |
| Nicotinic acid amide | 60 mg |
| Vitamin C calcium | 180 mg |
| Magnesium metasilicate aluminate | 135 mg |
| Polysolvate 60 | 95 mg |
| Propylene glycol | 12 mg |
| Wheat germ oil | 129 mg |

The foregoing compounds were weighed out and uniformly mixed. Then, 560 mg each of the resulting mixture was filled into soft elastic capsules or soft capsules to obtain 4 capsules.

EXAMPLE 14

(Formulation)

In 20 capsules,

| | |
|---|---|
| Zinc oxide | 6.3 mg |
| Linoleic acid | 5000 mg |
| γ-Linolenic acid | 1500 mg |
| Vitamin B$_2$ | 24 mg |
| Vitamin B$_6$ | 100 mg |
| Biotin | 0.5 mg |
| Pantothenic acid | 30 mg |
| Coix extract | 3000 mg |
| Nicotinic acid amide | 60 mg |
| Vitamin C | 180 mg |
| Magnesium metasilicate aluminate | 135 mg |
| Polysolvate 60 | 95 mg |
| Propylene glycol | 12 mg |
| Wheat germ oil | 129 mg |

The foregoing compounds were weighed out and uniformly mixed. Then, 560 mg each of the resulting mixture was filled into soft elastic capsules or soft capsules to obtain 20 capsules.

EXAMPLE 15

(Formulation)

In 19 capsules,

| | |
|---|---|
| Zinc oxide | 6.3 mg |
| Linoleic acid | 5000 mg |
| γ-Linolenic acid | 1500 mg |
| Ferrous fumarate | 15.2 mg |
| Magnesium carbonate | 200 mg |
| Coix extract | 2000 mg |
| Taurine | 500 mg |
| Royal jelly | 100 mg |
| Vitamin B$_2$ | 2.5 mg |
| Vitamin B$_6$ | 5 mg |
| Anhydrous caffeine | 50 mg |
| Magnesium metasilicate aluminate | 670 mg |
| Polysolvate 60 | 470 mg |
| Propylene glycol | 60 mg |
| Wheat germ oil | 127.5 mg |

The foregoing compounds were weighed out and uniformly mixed. Then, 560 mg each of the resulting mixture was filled into soft elastic capsules or soft capsules to obtain 19 capsules.

EXAMPLE 16

(Formulation)

| | |
|---|---|
| Zinc gluconate (trihydrate) | 1.57 g |
| Oil component * | 60.0 g |
| Sucrose fatty acid ester | 4.8 g |
| Glycerol monostearate | 7.2 g |
| Glycerol | 18.0 g |
| Ethanol | 20.0 g |
| Purified sucrose | 100.0 g |
| Butyl paraoxybenzoate | 0.1 g |
| Purified water to make the total volume | 1000 ml |

* Neutral lipid containing 5 g of DHA, 5 g of EPA, 5 g of DGLA and 5 g of Ara.

0.1 g of butyl paraoxybenzoate was added to 500 ml of purified water and dissolved therein with heating. Then, 100 g of purified sucrose was added thereto with stirring to obtain a homogenous mixture. After cooling, 1.45 g of zinc gluconate was added, followed by adjusting pH to 4.7 with a pH-adjusting agent to obtain a first mixture. Furthermore, 4.8 g of sucrose fatty acid ester, 7.2 g of glycerol monostearate, 18.0 g of glycerol, 20.0 g of ethanol and 60.0 g of oil component were mixed together with heating and uniform stirring, and after cooling, 100 ml of purified water was added thereto, and the mixture was homogeneously stirred in a pressure homogenizer to obtain an emulsion composition. The emulsion composition was mixed with the first mixture and homogenized in the pressure homogenizer, followed by addition of purified water to obtain 1000 ml of a liquid preparation.

EXAMPLE 17

(Formulation)

| | |
|---|---|
| Zinc sulfate (heptahydrate) | 88.5 mg |
| DHA | 500 mg |
| Magnesium metasilicate aluminate | 65 mg |
| Polysolvate 60 | 45 mg |
| Propylene glycol | 5 mg |

The foregoing compounds were weighed out and uniformly mixed. Then, the resulting mixture was evenly filled into soft elastic capsules or soft capsules, each of 400 mg to obtain 2 capsules.

EXAMPLE 18

(Formulation)

| | |
|---|---|
| Zinc gluconate (trihydrate) | 156.8 mg |
| Ara | 500 mg |
| Magnesium metasilicate aluminate | 65 mg |
| Polysolvate 60 | 45 mg |
| Propylene glycol | 5 mg |

The foregoing compounds were weighed out and uniformly mixed. Then, the resulting mixture was evenly filled into soft elastic capsules or soft capsules, each of 400 mg to obtain 2 capsules.

EXAMPLE 19

(Formulation)

| | |
|---|---|
| Zinc gluconate (trihydrate) | 156.8 mg |
| DGLA | 500 mg |
| Magnesium metasilicate aluminate | 65 mg |
| Polysolvate 60 | 45 mg |
| Propylene glycol | 5 mg |

The foregoing compounds were weighed out and uniformly mixed. Then, the resulting mixture was evenly filled into soft elastic capsules or soft capsules, each of 400 mg to obtain 2 capsules.

EXAMPLE 20

(Formulation)

| | |
|---|---|
| Zinc sulfate (heptahydrate) | 22.1 mg |
| DHA | 400 mg |
| EPA | 400 mg |
| Magnesium metasilicate aluminate | 65 mg |
| Polysolvate 60 | 45 mg |
| Propylene glycol | 5 mg |

The foregoing compounds were weighed out and uniformly mixed. Then, the resulting mixture was evenly filled into soft elastic capsules or soft capsules, each of 350 mg to obtain 3 capsules.

EXAMPLE 21

(Formulation)

| | |
|---|---|
| Zinc sulfate (heptahydrate) | 22.1 mg |
| Ara | 400 mg |
| DGLA | 400 mg |
| Magnesium metasilicate aluminate | 65 mg |
| Polysolvate 60 | 45 mg |
| Propylene glycol | 5 mg |

The foregoing compounds were weighed out and uniformly mixed. Then, the resulting mixture was evenly filled into soft elastic capsules or soft capsules, each of 350 mg to obtain 3 capsules.

EXAMPLE 22

(Formulation)

| | |
|---|---|
| Zinc gluconate (trihydrate) | 39.2 mg |
| DHA | 250 mg |
| EPA | 250 mg |
| Ara | 250 mg |
| DGLA | 250 mg |
| Vitamin $B_2$ | 24 mg |
| Vitamin $B_6$ | 100 mg |
| Nicotinic acid amide | 60 mg |
| Vitamin C | 180 mg |
| Magnesium metasilicate aluminate | 130 mg |
| Polysolvate 60 | 90 mg |
| Propylene glycol | 10 mg |

The foregoing compounds were weighed out and uniformly mixed. Then, the resulting mixture was evenly filled into soft elastic capsules or soft capsules, each of 350 mg to obtain 5 capsules.

EXAMPLE 23

(Formulation)

| | |
|---|---|
| Zinc sulfate (heptahydrate) | 22.1 mg |
| DHA | 250 mg |
| EPA | 250 mg |
| Vitamin $B_2$ | 24 mg |
| Vitamin $B_6$ | 100 mg |
| Nicotinic acid amide | 60 mg |
| Vitamin C calcium | 180 mg |
| Magnesium metasilicate aluminate | 98 mg |
| Polysolvate 60 | 68 mg |
| Propylene glycol | 8 mg |

The foregoing compounds were weighed out and uniformly mixed. Then, the resulting mixture was evenly filled into soft elastic capsules or soft capsules, each of 350 mg to obtain 3 capsules.

EXAMPLE 24

(Formulation)

| | |
|---|---|
| Zinc gluconate (trihydrate) | 39.2 mg |
| Ara | 250 mg |
| DGLA | 250 mg |
| Vitamin $B_2$ | 24 mg |
| Vitamin $B_6$ | 100 mg |
| Nicotinic acid amide | 60 mg |
| Vitamin C calcium | 180 mg |
| Magnesium metasilicate aluminate | 98 mg |
| Polysolvate 60 | 68 mg |
| Propylene glycol | 8 mg |

The foregoing compounds were weighed out and uniformly mixed. Then, the resulting mixture was evenly filled into soft elastic capsules or soft capsules, each of 400 mg to obtain 3 capsules.

EXAMPLE 25

(Formulation)

| | |
|---|---|
| Zinc sulfate (heptahydrate) | 0.44 g |
| Oil component * | 30.0 g |
| Vitamin $B_2$ | 0.24 g |
| Vitamin $B_6$ | 1.0 g |
| Biotin | 5.0 mg |
| Panthotenic acid | 0.30 g |
| Coix extract | 20.0 g |
| Nicotinic acid amide | 0.6 g |
| Vitamin C | 1.8 g |
| Sucrose fatty acid ester | 2.4 g |
| Glycerol monostearate | 3.6 g |
| Glycerol | 9.0 g |
| Ethanol | 10.0 g |
| Purified sucrose | 100.0 g |
| Butyl paraoxybenzoate | 0.1 g |
| pH-adjusting agent | appropriate amount |
| Perfume | trace |
| Purified water to make the total volume | 1000 ml. |

* Neutral lipid containing 5 g of DHA and 5 g of EPA.

0.1 g of butyl paraoxybenzoate was added to 500 ml of purified water and dissolved therein with heating, and 100 g of purified sucrose was added thereto with stirring to obtain a homogenous mixture. After cooling, 0.44 g of zinc sulfate was added, followed by adjusting pH to 4.7 with a pH-adjusting agent to obtain a first mixture. Furthermore, 2.4 g of sucrose fatty acid ester, 3.6 g of glycerol monostearate, 9.0 g of glycerol, 10.0 g of ethanol and 30.0 g of oil component were mixed with heating and uniform stirring, and after cooling, 100 ml of purified water was added thereto and the mixture was homogeneously stirred in a pressure homogenizer to obtain an emulsion composition. The emulsion composition was mixed with the first mixture and homogenized in the pressure homogenizer, followed by addition of purified water to obtain 1000 ml of a liquid preparation.

EXAMPLE 26

(Formulation)

| | |
|---|---|
| Zinc gluconate (trihydrate) | 0.39 g |
| Oil component * | 30.0 g |
| Iron ammonium citrate | 0.3 g |
| Magnesium aspartate | 5.95 g |
| Coix extract | 20.0 g |
| Taurine | 5.0 g |
| Royal jelly | 1.0 g |
| Vitamin $B_2$ | 25.0 mg |
| Vitamin $B_6$ | 50.0 mg |
| Anhydrous caffeine | 0.5 g |
| Sucrose fatty acid ester | 2.4 g |
| Glycerol monostearate | 3.6 g |
| Glycerol | 9.0 g |
| Ethanol | 10.0 g |
| Purified sucrose | 100.0 g |
| Butyl paraoxybenzoate | 0.1 g |
| pH-adjusting agent | appropriate amount |
| Perfume | trace |
| Purified water to make the total volume | 1000 ml |

* Neutral lipid containing 5 g of DGLA and 5 g of Ara.

0.1 g of butyl paraoxybenzoate was added to 500 ml of purified water and dissolved therein with heating, and 100 g of purified sucrose was added thereto with stirring to obtain a homogeneous mixture. After cooling, 0.39 g of zinc gluconate was added thereto, followed by adjusting pH to 4.7 with a pH-adjusting agent to obtain a first mixture. Furthermore, 2.4 g of sucrose fatty acid ester, 3.6 g of glycerol monostearate, 9.0 g of glycerol, 10.0 g of ethanol and 30.0 g of oil component were mixed with heating and uniform stirring, and after cooling, 100 ml of purified water was added thereto and the mixture was homogeneously stirred in a pressure homogenizer to obtain an emulsion composition. The emulsion composition was mixed with the first mixture and homogenized in the pressure homogenizer, followed by addition of purified water to obtain 1000 ml of a liquid preparation.

EXAMPLE 27

(Formulation)

| | |
|---|---|
| Zinc oxide | 6.3 mg |
| DHA | 500 mg |
| Magnesium metasilicate aluminate | 65 mg |
| Polysolvate 60 | 45 mg |
| Propylene glycol | 5 mg |

The foregoing compounds were weighed out and uniformed mixed. Then, the resulting mixture was evenly filled into soft elastic capsules or soft capsules, each of 400 mg to obtain 2 capsules.

TEST EXAMPLE 1

(Test materials)

① 4 week-old, male hairless rats were divided into 5 groups and fed with test feed having a zinc concentration of 3.5 ppm for 4 weeks.

Then, the rats were further bred with test feed containing 10% of evening primrose oil, perilla oil, Bio γ-linolenic acid oil, pine nut oil or corn oil and having a zinc concentration of 4.5 ppm for 4 weeks to observe skin states.

Control 1 were rats bred with test feed having a zinc concentration of 3.5 ppm for 4 weeks and further bred with test feed containing palm oil without linoleic acid, γ-linolenic acid and their esters as effective components and having a zinc concentration of 4.5 ppm for 8 weeks to observe skin states.

② Control 2 were rats bred at a zinc concentration of 20 ppm without oil feeding for 4 weeks to observe skin states.

(Test procedure)

① Observation of skin state:

After test breeding, a film was put over the back of rat to trace the inflamed parts, and then weight of inflamed parts was measured to calculate the inflamed area.

② Quantitative determination of essential fatty acids:

1.5 ml of an ice-cooled aqueous 2M KCl/0.1M EDTA solution was added to 0.5 ml of plasma, and further 5 ml of methanol and 2.5 ml of chloroform were added thereto, followed by mixing with a Boltic mixer for 2 minutes. Then, the resulting mixture was centrifuged at 3000 rpm for 10 minutes to separate it into two layers. The lower chloroform layer was washed with 2M KCl and then with water and centrifuged. Then, the chloroform layer was concentrated to dryness at 35° C. in a nitrogen gas stream, and after immediate addition of 20 µl of chloroform (containing 0.01 BHT), preserved at –20° C.

Analysis was carried out by gas chromatography with a column (megapore column DB-23 made by J & W).

③ Quantative determination of skin zinc concentration:

About 20 mg of epidermis was exactly weighed out into a desalted Teflon crucible and subjected to an acid decomposition under pressure in 1 ml of concentrated nitric acid at 100° C. for 4 hours to obtain test samples. Quantitative determination of the metal was carried out by a flame method using an atomic absorption spectrometry (model Hitachi 8100).

(Results)

Figure 2:
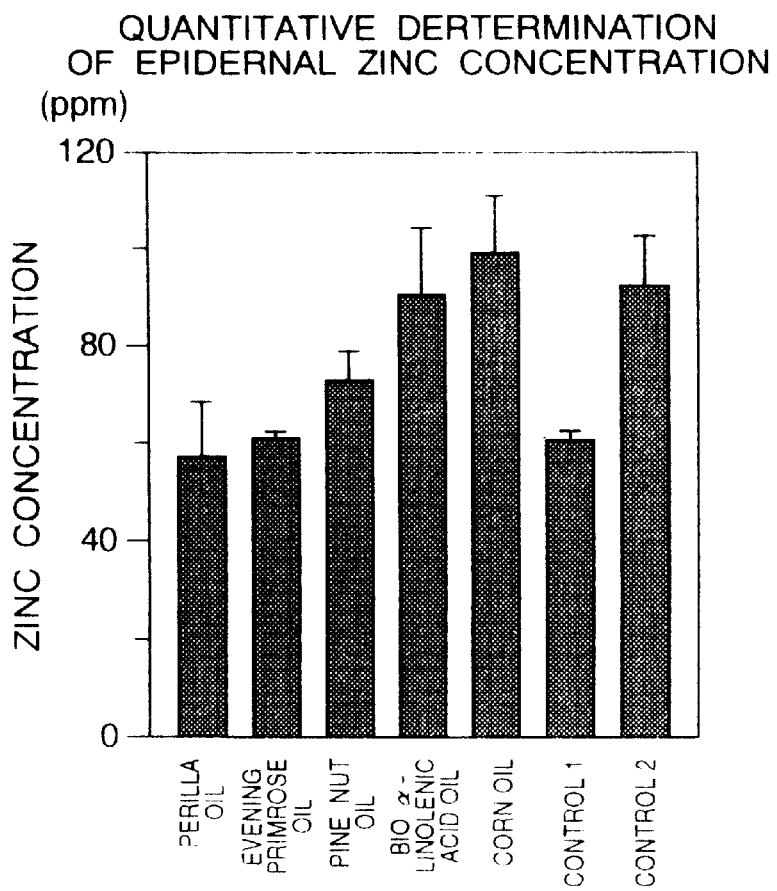
FIG. 2 is a diagram showing correlations between epidermal zinc concentration (ppm) on the axis of ordinate and increase ratio of epidermal zinc concentration as determined for individual drugs on the axis of abscissa.

Test results are shown in Tables 1 and 2, and FIGS. 1 and 2.

TABLE 1

| Fatty acid | Perilla oil | Evening primrose oil | Pine nut oil | Bio γ-linolenic acid oil | Corn oil | Control 1 | Control 2 |
|---|---|---|---|---|---|---|---|
| Linoleic acid (18:2 ω6) | 28.4 | 43.06 | 28.44 | 30.92 | 35.10 | — | — |
| γ-Linolenic acid (18:3 ω6) | — | 10.42 | — | 5.09 | — | — | — |
| γ-Linolenic acid (18:3 ω3) | 19.70 | 7.68 | 7.68 | 7.68 | 9.60 | — | — |
| Inflamed area | 18.2 | 17.9 | 2.6 | 2.1 | 0.9 | 15.0 | 0.9 |
| Zn concentration as fed | 3.5 ppm for 4 weeks (former half period) 4.5 ppm for 4 weeks (latter half period) | | | | | | 20 ppm (for 8 weeks) |

TABLE 2

| Fatty acid | Epidermal zinc concentration (ppm) |
|---|---|
| Perilla oil | 56.8 ± 11.4 |
| Evening primrose oil | 60.6 ± 1.3 |
| Pine nut oil | 72.3 ± 6.3 |
| Bio γ-linolenic acid oil | 89.7 ± 13.9 |
| Corn oil | 98.5 ± 11.4 |
| Control 1 | 59.3 ± 2.1 |
| Control 2 | 91.3 ± 10.2 |

Controls 1 and 2 are the same as in Table 1.

Rats suffering from skin diseases caused by breeding with zinc-deficient feed (Zn: 3.5 ppm) for 4 weeks were bred with low-zinc feeds (Zn: 4.5 ppm) containing one of 5 kinds of oils having different fatty acid compositions. As a result, Bio γ-linolenic acid oil containing 26.5 to 52.8% of linoleic acid and 5.0 to 7.6% of γ-linolenic acid could improve the skin inflammation, as compared with control 1 (low-zinc feed containing palm oil).

Pine nut oil and corn oil containing no γ-linolenic acid, but containing 26.5 to 52.8% of linoleic acid could also improve the skin inflammation, as compared with control 1. Corn oil showed an improvement equivalent to that of control 2 (bred with 20 ppm Zn).

Evening primrose oil containing 26.7 to 52.8% of linoleic acid and over 8% of γ-linolenic acid showed no improvement of skin inflammation, as compared with control 1. Perilla oil containing linoleic acid within the range and a large amount of α-linolenic acid showed no improvement of skin inflammation, as compared with control 1.

In the quantitative determination of epidermal zinc concentration, oil, showing a smaller inflamed area and thus a tendency of improvement had a tendency of higher epidermal zinc concentration.

TEST EXAMPLE 2

(Test materials)

① 4-week old, male hairless rats were divided into two groups, and one group was bred with test feed having a zinc concentration of 3.5 ppm and containing DHA (2.72 mg/100 mg feed) for 4 weeks, while other group was bred with test feed containing EPA (2.56 mg/100 mg feed) for 4 weeks, to observe skin state.

② Control 1 was bred with test feed having a zinc concentration of 3.5 ppm and containing 10% of corn oil (without EPA and DHA) for 4 weeks to observe skin state.

③ Control 2 was bred with test feed having a zinc concentration of 20 ppm and 10% of corn oil (without EPA and DHA) for 4 weeks to observe skin state.

(Test procedure)

① Transepidermal water loss (TEWL):

Transepidermal water loss was measured by an impedance meter model SKICON-200 (made by IBS Co.). Degree of improvement of rough, dry skin was judged from results of TEWL and visual observation of deterioration degree of skin state (for those with recognized inflamed sites).

② Quantitative determination of epidermal zinc concentration:

About 20 mg of epidermis was exactly weighed out into a desalted Teflon crucible and subjected to an acid decomposition under pressure in 1 ml of concentrated nitric acid at 100° C. for 4 hours to obtain test samples. Quantative determination of the metal was carried out by a flame procedure using an atomic absorption spectrometry (model Hitachi 8100).

③ Quantitative determination of linoleic acid in acylceramide:

Separation of epidermis was carried out by a heat treatment method; extraction of lipid by a Folch method; and fractionation of ceramide by a thin layer chromatography. Concentration of fatty acid (linoleic acid) in acylceramide closely relates to moisture-maintaining ability and barrier function of keratin, and thus was measured as an indicator of rough, dry skin symptom [B. B. A, 834 (1985) 357–363, Elsevier].

Quantitative determination of fatty acid in acylceramide was carried out by gas chromatography after the hydrolysis with methanol/NaOH and methyl esterification with hydrochloric acid and methanol.

(Test results)

Figure 3:
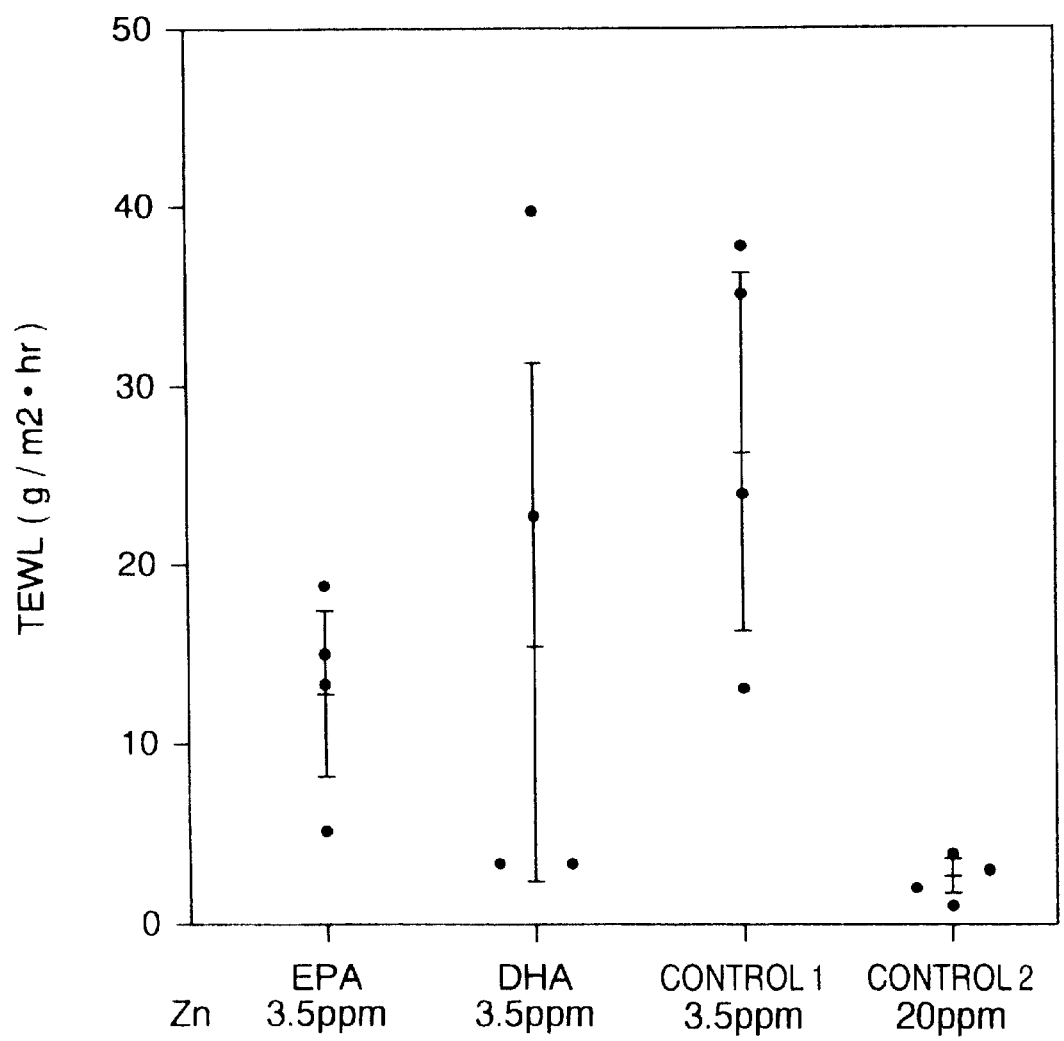
FIG. 3 is a diagram showing correlations between TEWL [transepidemal water loss ($g/m^2 \cdot hr$)] on the axis of ordinate and suppression ratio of transepidermal water loss as determined for individual drugs on the axis of abscissa.
Figure 4:
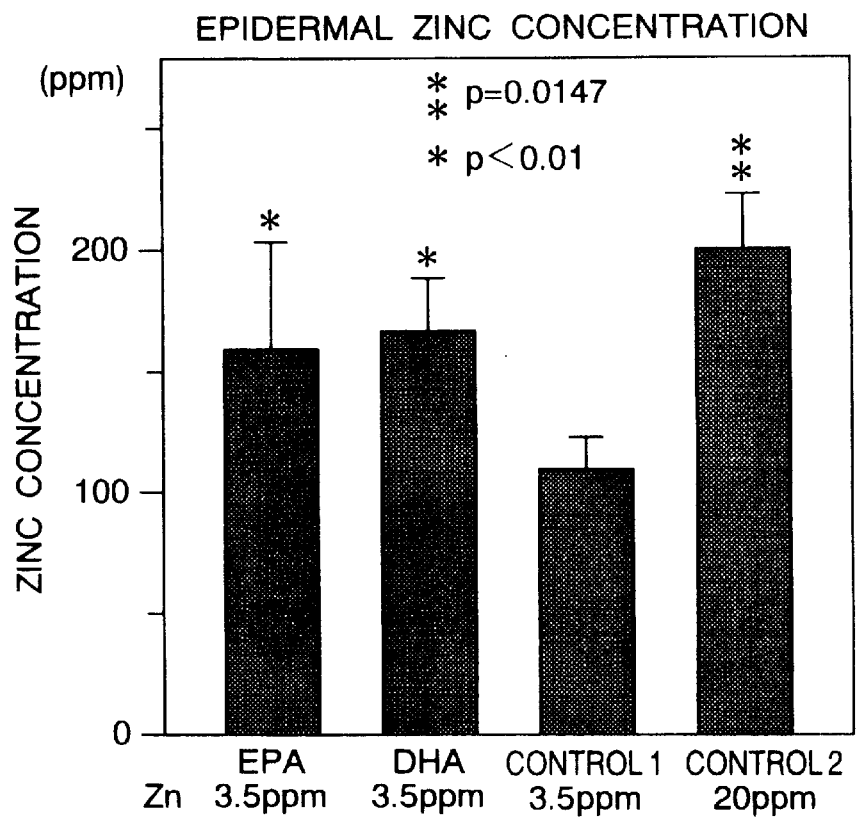
FIG. 4 is a diagram showing correlations between epidermal zinc concentration (ppm) on the axis of ordinate and increase ratio of epidermal zinc concentration as determined for individual drugs on the axis of abscissa.
Figure 5:
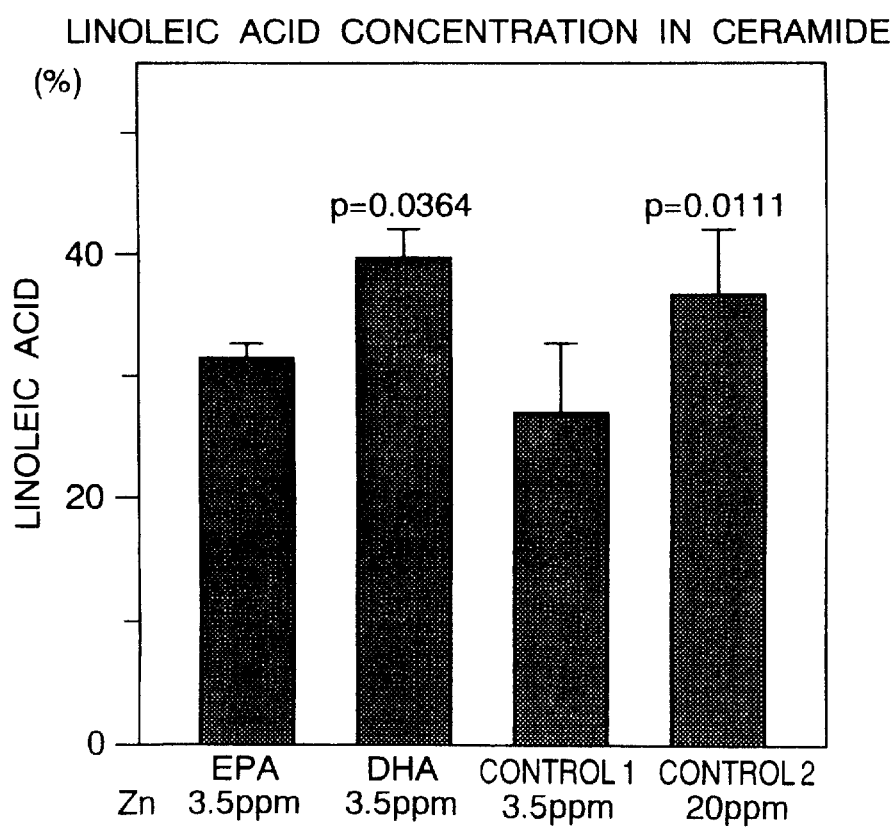
FIG. 5 is a diagram showing correlations between linoleic acid concentration (%) in ceramide on the axis of ordinate and increase ratio of linoleic acid concentration as determined for individual drugs on the axis of abscissa.

Test results are shown in Tables 3, 4 and 5 and FIGS. 3, 4 and 5.

TABLE 3

Average TEWL value and effect on improvement of rough, dry skin

| Sample | Average TEWL value (g/m².hr) | Degree of improvement |
|---|---|---|
| EPA (Zn:3.5 ppm) | 13.0 ± 5.0 | 25% (1/4) |
| DHA (Zn:3.5 ppm) | 17.2 ± 15.4 | 50% (2/4) |
| Control 1 (Zn:3.5 ppm) | 27.5 ± 9.8 | 0% (0/4) |
| Control 2 (Zn:20 ppm) | 2.5 ± 1.1 | 100% (4/4) |

TABLE 4

Epidermal zinc concentration

| Sample | Epidermal zinc concentration (ppm) |
| --- | --- |
| EPA (Zn: 3.5 ppm) | 158.8 ± 42.2 |
| DHA (Zn: 3.5 ppm) | 166.1 ± 20.9 |
| Control 1 (Zn: 3.5 ppm) | 108.9 ± 11.6 |
| Control 2 (Zn: 20 ppm) | 198.0 ± 23.5 |

TABLE 5

Linoleic acid concentration in ceramide

| Sample | Linoleic acid concentration (ppm) |
| --- | --- |
| EPA (Zn: 3.5 ppm) | 30.9 ± 1.48 |
| DHA (Zn: 3.5 ppm) | 39.3 ± 2.16 |
| Control 1 (Zn: 3.5 ppm) | 26.6 ± 5.60 |
| Control 2 (Zn: 20 ppm) | 36.3 ± 2.68 |

We claim:

1. An oral dermatitis-curing composition comprising an orally effective amount of (A) a zinc compound and (B) docosahexaenoic acid or an ester thereof as effective components.

* * * * *